United States Patent
Leftheris

[11] Patent Number: 5,929,077
[45] Date of Patent: Jul. 27, 1999

[54] THIOPROLINE-CONTAINING INHIBITORS OF FARNESYL PROTEIN TRANSFERASE

[76] Inventor: Katerina Leftheris, 92 Richmond Dr., Skillman, N.J. 08558

[21] Appl. No.: 08/953,117

[22] Filed: Oct. 17, 1997

Related U.S. Application Data

[60] Provisional application No. 60/029,894, Nov. 8, 1996.
[51] Int. Cl.[6] ........................ A61K 31/495; C07D 403/02; C07D 241/02
[52] U.S. Cl. ........................ 514/255; 514/212; 514/227.8; 514/235.8; 514/248; 514/249; 514/252; 540/524; 540/598; 544/58.1; 544/60; 544/121; 544/235; 544/238; 544/283; 544/335; 544/353; 544/357; 544/360; 544/364; 544/365; 544/372; 544/386; 544/387; 544/388
[58] Field of Search ........................ 514/212, 227.8, 514/235.8, 248, 249, 252, 255; 540/524, 598; 544/58.1, 60, 121, 235, 238, 283, 335, 353, 357, 360, 364, 365, 372, 386, 387, 388

Primary Examiner—Mukund J. Shah
Assistant Examiner—Brenda Coleman
Attorney, Agent, or Firm—Frank P. Hoffman

[57] ABSTRACT

Inhibition of farnesyl transferase, which is an enzyme involved in ras oncogene expression, is effected b

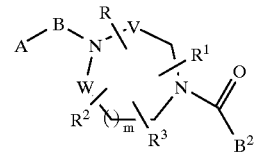

its enantiomers, diastereomers, and pharmaceutically acceptable salts and solvates thereof.

18 Claims, No Drawings

THIOPROLINE-CONTAINING INHIBITORS OF FARNESYL PROTEIN TRANSFERASE

This application claims priority from U.S. provisional application 60/029,894, filed Nov. 8, 1996.

FIELD OF THE INVENTION

This invention relates to compounds that inhibit farnesyl-protein transferase and Ras protein farnesylation, thereby making them useful as anti-cancer agents. The compounds are also useful in the treatment of diseases, other than cancer, associated with signal transduction pathways operating through Ras and those associated with CAAX-containing proteins other than Ras that are also post-translationally modified by the enzyme farnesyl protein transferase. The compounds may also act as inhibitors of other prenyl transferases, and thus be effective in the treatment of diseases associated with other prenyl modifications of proteins.

BACKGROUND OF THE INVENTION

The mammalian ras gene family comprises three genes: H-ras, K-ras and N-ras. The Ras proteins are a family of GTP-binding and hydrolyzing proteins that regulate cell growth and differentiation. Overproduction of normal Ras proteins or mutations that inhibit their GTPase activity can lead to uncontrolled cell division.

The transforming activity of Ras is dependent upon localization of the protein to plasma membranes. This membrane binding occurs via a series of post-translational modifications of the cytosolic Ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The Ras C-terminus contains a sequence motif termed a "Cys-Aaa$_1$-Aaa$_2$-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thioether linkage.

BRIEF DESCRIPTION OF THE INVENTION

In accordance with the present invention, a compound of the formula I

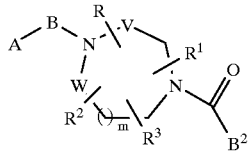

its enantiomers and diastereomers, and pharmaceutically acceptable salts, prodrugs and solvates thereof inhibit S-farnesyl protein transferase which is an enzyme involved in Ras oncogene function. In formula I and throughout this specification, unless otherwise specified, the symbols are defined as follows: A is

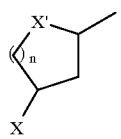

optionally substituted, at any available position or positions on the ring, with one or more of the following substituents, halo, alkyl, alkoxy, aryl, hydroxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl or alkoxycarbonyl;

B is —CH$_2$— or —C(O)—;

B$^2$ is alkyl, aryl or heterocycle;

V and W are each, independently, —CH$_2$— or —C(O)—;

X is —SH, —OH or —NHR$^6$;

X' is —NR$^7$—, —CH$_2$— or —CH(NHR$^8$)—;

R, R$^1$, R$^2$ and R$^3$ are each independently, hydrogen, alkyl, alkenyl, alkynyl, aryl, heterocycle, —C(O)NR$^4$R$^5$, or —C(O)OR$^4$; or any two of R, R$^1$, R$^2$ and R$^3$, if present, may also be alkylene attached to the same carbon atom forming a spiro ring;

R$^4$ and R$^5$ are each independently selected from hydrogen, hydroxyl, alkyl, cycloalkyl, heterocycle, aryl, aroyl, heteroaroyl, arylsulfonyl or heteroarylsulfonyl; or R$^4$ and R$^5$ may together form a 5- to 7-membered saturated ring with the atom to which they are attached; said ring being optionally substituted with halogen, hydroxy, alkoxy, oxo, nitro, cyano, —C(O)H, —C(O)OH and the like;

R$^6$, R$^7$ and R$^8$ are each independently, hydrogen or alkyl;

m is an integer from 0 to 1; and n is an integer from 1 to 2.

DETAILED DESCRIPTION OF THE INVENTION

Definition of Terms

Listed below are definitions of various terms used to describe this invention. These definitions apply to the terms as they are used throughout this specification, unless otherwise limited in specific instances, either individually or as part of a larger group.

The term "alkyl" refers to optionally substituted straight or branched chain hydrocarbon groups having 1 to 20 carbon atoms, preferably 1 to 8 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpenthyl, octyl and the like. The term "alkyl" also includes substituted alkyl groups. Substituted alkyl groups refer to alkyl groups substituted by one or more of the following groups: halo (such as CCl$_3$ or CF$_3$), hydroxy, —OR$^{11}$, cycloalkyl, alkanoyl, alkanoyloxy, amino, alkylamino, dialkylamino, alkanoylamino, thiol, alkylthio, alkylthiono, alkylsulfonyl, arylsulfonyl, heteroarylsulfonyl, sulfonamido, nitro, cyano, carboxy, carbamyl, alkoxycarbonyl, aryl, aralkoxy, phenyl, substituted phenyl, guanidino, indolyl, imidazolyl, furyl, thienyl, thiazolyl, pyrrolidyl, pyridyl, pyrimidyl and the like.

The term "lower alkyl" refers to those alkyl groups as described above having 1 to 4 carbon atoms.

The term "halogen" or "halo" refers to fluorine, chlorine, bromine and iodine.

The term "alkenyl" refers to any of the above alkyl groups having at least 2 carbon atoms and further containing at least one carbon to carbon double bond. Groups having two to four carbon atoms are preferred.

The term "alkynyl" refers to any of the above alkyl groups having at least two carbon atoms and further containing at least one carbon to carbon triple bond. Groups having two to four carbon atoms are preferred.

The term "alkylene" refers to a straight chain bridge of 1 to 6 carbon atoms connected by single bonds (e.g., —(CH$_2$)$_x$— wherein x is 1 to 6), which may be substituted with 1 to 3 lower alkyl groups.

The term "cycloalkyl" refers to cyclic hydrocarbon groups of 3 to 8 carbon atoms.

The term "alkoxy" refers to alkyl—O—.

The term "alkanoyl" refers to alkyl—C(O)—.

The term "alkanoyloxy" refers to alkyl—C(O)—O—.

The terms "alkylamino" and "dialkylamino" refer to (alkyl)NH— and (alkyl)$_2$N—, respectively.

The term "alkanoylamino" refers to alkyl—C(O)—NH—.

The term "alkylthio" refers to alkyl—S—.

The term "alkylthiono" refers to alkyl—S(O)—.

The term "alkylsulfonyl" refers to alkyl—S(O)$_2$—.

The term "carbamyl" refers to —C(O)NR$^4$R$^5$.

The term "alkoxycarbonyl" refers to alkyl—O—C(O)—.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents such as alkyl, halo, hydroxy, alkoxy, alkanoyl, alkanoyloxy, amino, alkylamino, dialkylamino, alkanoylamino, thiol, alkylthio, nitro, cyano, carboxy, carboxyalkyl, carbamyl, alkoxycarbonyl, alkylthiono, alkylsulfonyl, sulfonamido, heterocyclo and the like.

The term "aralkyl" refers to an aryl group bonded directly through an alkyl group, such as benzyl.

The term "aralkoxy" refers to an aryl group bonded directly through an alkoxy group.

The term "arylsulfonyl" refers to aryl—S(O)$_2$—.

The term "aroyl" refers to aryl—C(O)—.

The term "heterocycle" refers to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), 3,4-dihydro-4-oxo-quinazolinyl) and the like.

Exemplary tricyclic heterocyclic groups include carbazolyl, benzidolyl, phenanthrolinyl, acridinyl, phenanthridinyl, xanthenyl and the like.

The term "heterocycle" also includes substituted heterocycle groups. Substituted heterocycle groups refer to heterocycle groups substituted with 1, 2 or 3 of the following:

(a) alkyl;

(b) hydroxy (or protected hydroxy);

(c) halo;

(d) oxo (i.e.=O);

(e) amino, alkylamino or dialkylamino;

(f) alkoxy;

(g) cycloalkyl;

(h) carboxy;

(i) heterocyclooxy;

(j) alkoxycarbonyl, such as unsubstituted lower alkoxycarbonyl;

(k) carbamyl, alkylcarbamyl dialkylcarbamyl;

(l) mercapto;

(m) nitro;

(n) cyano;

(o) sulfonamido, sulfonamidoalkyl or sulfonamidodialkyl;

(p) aryl;

(q) alkylcarbonyloxy;

(r) arylcarbonyloxy;

(s) arylthio;

(t) aryloxy;

(u) alkylthio;

(v) formyl;

(w) arylalkyl; or aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" refers to an aromatic heterocycle.

The term "heteroarylsulfonyl" refers to heteroary—S(O)$_2$—.

The term "heteroaroyl" refers to heterocyclo—C(O)—.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compound I with the desired ion in a medium in which the salt precipitates or in an aqueous medium followed by evaporation. Other salts can be formed as known to those having ordinary skill in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

A compound of the formula I may also have prodrug forms. Any compound that will be converted in vivo to provide the bioactive agent (i.e., the compound of formula I) is a prodrug within the scope and spirit of the invention.

Various forms of prodrugs are well known in the art. For examples of such prodrug derivatives, see:

a) Anne H. Kahns and Hans Bundgaard, *International Journal of Pharmaceutics*, 6 (1990), p. 193–205.

b) *Design of Prodrugs*, edited by H. Bundgaard, (Elsevier, 1985) and *Methods in Enzymology*, Vol. 42, 309–396, edited by K. Widder et al. (Academic Press, 1985);

c) *A Textbook of Drug Design and Development*, edited by Krogsgaard-Larsen and H. Bundgaard, Chapter 5, "Design and Application of Prodrugs," by H. Bundgaard, 113–191 (1991);

d) H. Bundgaard, *Advanced Drug Delivery Reviews*, 8, 1–38 (1992);

e) H. Bundgaard et al., *Journal of Pharmaceutical Sciences*, 77,285 (1988); and f) N. Kakeya et al., *Chem Pharm Bull*, 32, 692 (1984).

It should further be understood that solvates (e.g., hydrates) of the compounds of formula I are also within the scope of the present invention. Methods of solvation are generally known in the art.

Use and Utility

The compounds of formula I are inhibitors of S-farnesyl protein transferase. They are thus useful in the treatment of a variety of cancers, including (but not limited to) the following:

carcinoma, including that of the bladder, breast, colon, rectum, kidney, liver, lung, ovary, pancreas, stomach, cervix, thyroid and skin;

hematopoietic tumors of lymphoid lineage, including acute lymphocytic leukemia, B-cell lymphoma and Burkitts lymphoma;

hematopoietic tumors of myeloid lineage, including acute and chronic myelogenous leukemias and promyelocytic leukemia;

tumors of mesenchymal origin, including fibrosarcoma and rhabdomyosarcoma;

tumors of the central and peripheral nervous system; and other tumors, including melanoma, seminoma, tetratocarcinoma, neuroblastoma, astrocytoma and glioma.

The compounds of formula I are especially useful in treatment of tumors having a high incidence of ras involvement, such as colon, lung, and pancreatic tumors; as well as tumors adversely affected by inhibition of farnesyl transferase or prenyl transferase. By the administration of a composition having one (or a combination) of the compounds of this invention, development of or progression of tumors in a mammalian host is reduced.

Compounds of formula I may also be useful in the treatment of diseases other than cancer that may be associated with signal transduction pathways operating through ras, e.g., neuro-fibromatosis, atherosclerosis, pulmonary fibrosis, arthritis, psoriasis, glomerulonephritis, polycystic kidney disease, restenosis following angioplasty or vascular surgery, hypertrophic scar formation, endotoxic shock and autoimmune and inflammatory diseases such as rheumatoid arthritis, asthma, urticaria, angioedema, systemic sclerosis and scleroderma, vasculitis, gout, inflammatory lung disease (emphysema, bronchitis, fibrosis), adult respiratory distress syndrome (ARDS), Lupus erythematosus, arteriosclerosis, inflammatory bowel disease (Crohn's disease, ulcerative colitis), periodontal disease, multiple sclerosis, myasthemia gravis, graft vs. host disease, transplantation rejection, Sjogren's disease, Graves disease and type 1 diabetes. Compounds of formula I may be useful as anti-fungal agents.

Compounds of formula I may also be useful in the treatment of diseases associated with farnesyl transferase substrates other than ras (e.g., nuclear lamins and transducin) that are also post-translationally modified by the enzyme farnesyl protein transferase.

Compounds of I may also act as inhibitors of other prenyl transferases (e.g., geranylgeranyl transferase I and II), and thus be effective in the treatment of diseases associated with other prenyl modifications (e.g., geranylgeranylation) of proteins (e.g., the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection (J. S. Glen et al., *Science*, 256, 1331 (1992)).

The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatments, including radiation when a combination formulation is inappropriate.

Farnesyl transferase assays were performed as described in V. Manne et al., *Drug Development Research*, 34, 121–137 (1995). The compounds of Examples 1–8 inhibited farnesyl transferase with $IC_{50}$ values between 0.1 nM and 10 mM.

The compounds of this invention may be formulated with a pharmaceutical vehicle or diluent for oral, parenteral, intravenous, subcutaneous, rectal, vaginal or topical administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 50 mg/kg/day, preferably less than 50 mg/kg/day, in a single dose or in 2 to 4 divided doses.

Compounds of formula I where B is $CH_2$ may be prepared by coupling compounds of formula II

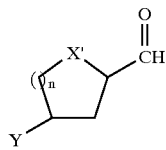

where Y is a protected thiol, protected alcohol or protected amine with compounds of formula III

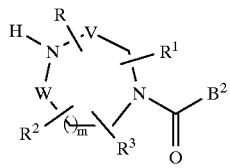

by reductive amination using a reducing agent such as sodiumtriacetoxyborohydride or sodium cyano borohydride to form compounds of formula IV

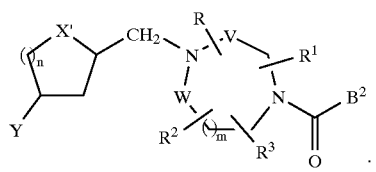

Compounds of formula IV are deprotected to provide compounds of formula I where B is $CH_2$ using standard methods known in the literature (*Protecting Groups in Organic Synthesis*, 2nd Edition, Theodora Green, Peter Wuts, John Wiley & Sons, Inc. 1991).

Alternatively compounds of formula IV where Y is a trityl S- can be deprotected using acidic conditions such as 50% trifluoroacetic acid in methylene chloride in the presence of a scavenger such as triethylsilane.

Alternatively, compounds of formula I where X is OH or —$NHR^6$ may also be prepared by reductive amination using compounds of formula II and III and hydrogen with a catalyst such as palladium on carbon or palladium hydroxide on carbon.

Compounds of formula I where B is C(O) can be prepared by coupling compounds of formula V

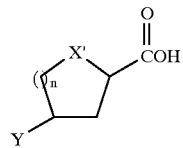

with a compound of formula III in the presence of a coupling agent (e.g., dicyclohexylcarbodiimide (DCC)) to form compounds of formula VI

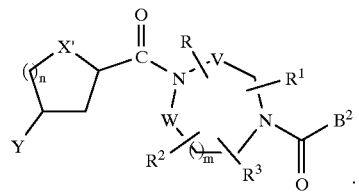

Compounds of formula VI are converted to compounds of formula I where B is C(O) by deprotecting using standard methods found in the literature.

Compounds of formula II and V are prepared by methods known in the art. See, for example, V. Eskwarakrishnan and L. Field, *J. Org. Chem.*, 46, 4182 (1981); D. Papaioannou et al., Acta Chemica Scandinavia, 44, 243 (1990); A. Meyers, *Org. Syn.*, 51, 103 (1971); T. Rosen et al., *Synthesis*, 40, (1988); C. Agami et al., *Tetrahedron*, 48, 431 (1992); Y. Ueda and V. Vinet, *Can. J. Chem.*, 64, 2184 (1986); Sinagawa et al., *J. Antibiotico*, 43 (1990) p. 519–532; and EP 696593-A2.

Compounds of formula III where V and W are —$CH_2$—, m=0, $B^2$ is aryl, $R^1$, $R^2$ and $R^3$ are each hydrogen, R is attached to V and is alkyl (other than arylsulfonyl or heteroarylsulfonyl substituted alkyl) are prepared by coupling a compound of formula VII

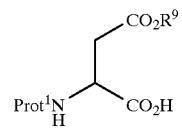

wherein $R^9$ is alkyl, arylalkyl or aryl and $Prot^1$ is an amine protecting group (e.g., t-butyloxycarbonyl (BOC), benzyloxycarbonyl (Cbz) and the like): in the presence of a coupling agent (e.g., dicyclohexylcarbodiimide (DCC)) with a carboxylic acid derivative of the formula VIII

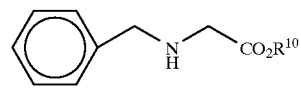

wherein $R^{10}$ is alkyl, arylalkyl or aryl, to form a compound of the formula

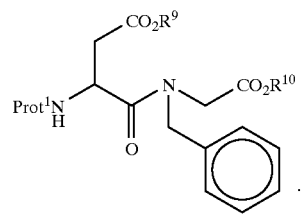

Compounds of formula IX can then be treated with a suitable N-deprotecting agent (e.g., HCl for BOC) and cyclized to provide a compound of formula X

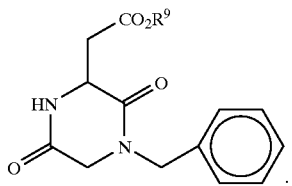

A compound of formula X can be reduced with a reducing agent (e.g., lithium aluminum hydride (LiAlH$_4$)) to form the compound of the formula XI

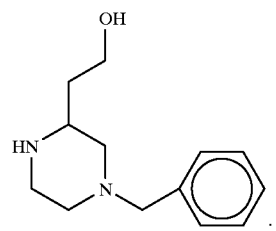

The compound of formula XI can then be protected with a protecting agent (e.g., di-t-butyloxy dicarbonate) to form a compound of the formula XII

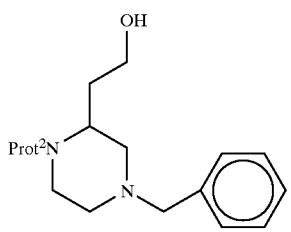

wherein Prot$^2$ is a suitable protecting group, (e.g. t-butyloxycarbonyl).

The hydroxy group in the compound of formula XII can then be alkylated under basic conditions (e.g., sodium hydride with a compound of formula XIIa

R$^{11}$—L where L is a leaving group, for example a halide or sulfonyl ester; and R$^{11}$ is alkyl, alkenyl, alkynyl, cycloalkyl, aryl, aroyl, heteroaroyl, arylsulfonyl, heteroarylsulfonyl, heterocycle or —C(O)NR$^4$R$^5$) to form a compound of the formula XIII

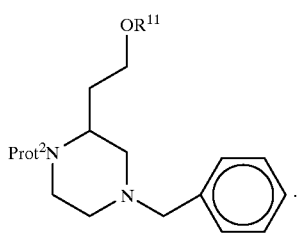

Compounds of the formula XIII can then be hydrogenated using a catalyst in the presence of hydrogen (e.g., palladium/carbon/hydrogen) to form a compound of the formula XIV

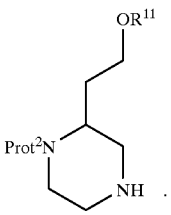

A compound of formula XIV can then be coupled with a compound of the formula XIVa ArCO$_2$H wherein Ar is an aryl group, in the presence of a coupling agent such as DCC to provide a compound of the formula XV

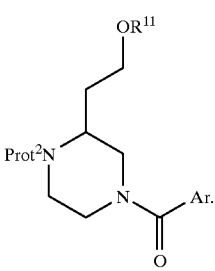

A compound of formula XV can then be deprotected with an acid e.g., HCl, to provide a compound of the formula XVI

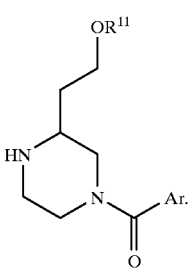

Compounds of formula XVI are compounds of formula III where V and W are —CH$_2$—, m=0, B$^2$ is aryl, R$^1$, R$^2$ and R$^3$ are each hydrogen and R is attached to V and is alkyl having an —OR$^{11}$ substituent. Compounds of formula XVI can be modified as known by those having ordinary skill in the art to other compounds of formula III where R is a different alkyl group, other than arylsulfonyl or heteroarylsulfonyl substituted alkyl.

Compounds of formula III where V and W are —CH$_2$—, m=0, B$^2$ is aryl, R$^1$, R$^2$ and R$^3$ are each hydrogen, R is attached to V and is an arylsulfonyl or heteroarylsulfonyl substituted alkyl can be prepared by deprotecting compounds of formula XII (with e.g. NCl) to form compounds of formula XVII

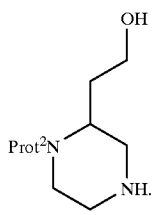

Compounds of formula XVII can be coupled to a compound of formula XIVa in the presence of a coupling agent such as DCC to form compound of formula XVIII

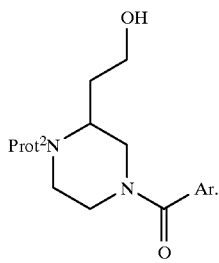

Treatment of a compound of formula XVIII with an aryldisulfide such as diphenyl disulfide in the presence of a trialkyl phosphene such as tri n-butylphosphene followed by oxidation to the sulfonyl using an oxidizing agent such as the magnesium salt of monoperoxyphthalic acid provides compounds of formula XIX

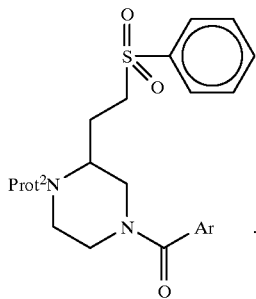

A compound of formula XIX can be deprotected (with e.g. HCl) to provide a compound of formula XX

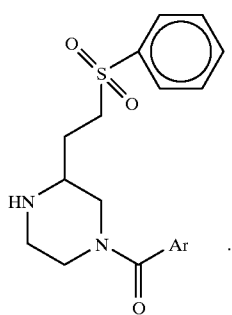

Compounds of formula XX are compounds of formula III where V and W are —CH$_2$—, m=0, B$^2$ is aryl, R$^1$, R$^2$ and R$^3$ are each hydrogen and R is attached to V and is an arylsulfonyl substituted alkyl. Compounds of formula XX can be modified as known by those having ordinary skill in the art to other compounds of formula III where R is a different arylsulfonyl or heteroarylsulfonyl substituted alkyl.

Other compounds of formula III can be prepared by modification of the procedures described herein.

Compounds of formula VII, VIII, XIIa and XIVa can be prepared from commercially available materials or are commercially available.

Protecting groups as used herein may be used in the above processes with amino acids having reactive functionalities, such as hydroxyl, carboxyl, amino, mercapto, guanidino, imidazolyl, indolyl and the like. The particular protecting groups used for any amino acid residues depend upon the sidechains to be protected and are generally known in the art. Exemplary sidechain protecting groups include acetyl, benzoyl, benzyl, t-butyl and the like for hydroxyl; cyclohexyl, benzyl, methyl, ethyl, t-butyl and the like for carboxyl; benzyl, 4-methylbenzyl, 4-methoxybenzyl, acetyl, acetamidomethyl, triphenylmethyl (trityl) and the like for mercapto; t-butoxylcarbonyl (Boc), benzyloxylcarbonyl (Cbz), N-[(9H-Fluoren-9-ylmethoxy)carbonyl] (Fmoc), phthaloyl (Pht), p-toluenesulfonyl (Tos), trifluoroacetyl, 2-(trimethylsilyl)ethoxycarbonyl (Teoc) and the like for amino; 2,4-dinitrophenyl, benzyloxymethyl, Tos, Boc, trityl and the like for imidazolyl; formyl, Cbz, Teoc, 2,2,2-trichloroethyl carbamate (TROC) and the like for indolyl; and tosyl, nitro, bis(1-adamantyloxycarbonyl) and the like for guanidino.

Side-chain protecting groups may be removed, if desired, by, for example, treatment with one or more deprotecting agents in an inert solvent or solvent mixture. For examples of protecting groups and suitable deprotecting agents, see M. Bodansky and A. Bodansky, "The Practice of Peptide Synthesis",Springer-Verlag, Inc. (1984); and T. W. Greene and P. G. M. Wuts, "Protective Groups in Organic Synthesis", Second Edition, John Wiley & Sons, New York, 1991.

For additional examples of protecting groups (as well as means of formation and eventual deprotection), see T. W. Greene and P. G. M. Wuts, "Protective Groups in Organic Synthesis", Second Edition, John Wiley & Sons, New York, 1991.

A variety of coupling agents may be used for the coupling of compounds of formula VII with VIII to form compounds of formula IX, including 1-(3-dimethyl-aminopropyl)-3-ethyl-carbodiimide hydrochloride (EDC) with 1-hydroxybenzotriazole (HOBT), dicyclohexyl-carbodiimide (DCC) with HOBT, benzotriazol-1-yloxy-tris (dimethylamino)phosphonium hexafluoro-phospate (BOP) with or without HOBT, carbonyldiimidazole (CDI), bis(2-oxo-3-oxazolidinyl)phosphinic chloride (BOP chloride), isopropylchloroformate (IPCF), bromo-tris-pyrrolidino-phosphonium hexafluorophosphate (ByBroP) and the like.

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

[2S-[2a(R*),4a]]-1-[(4-Mercapto-2-pyrrolidinyl)methyl]-2-(2-methoxyethyl)-4-(1-naphthalenylcarbonyl)piperazine, trifluoroacetate

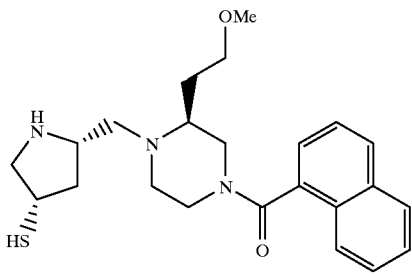

A. 1-Benzyl-3(S)-cyclohexyloxycarbonylmethylpiperazine-2,5-dione

Boc-L-aspartic acid b-cyclohexyl ester (33 g, 105 mmol) was added to a 0.143 M solution of dicyclohexylcarbodiimide (21.6 g, 105 mmol) in methylene chloride (730 mL) at 0° C. The resulting slurry was stirred for 5 minutes, and ethyl N-benzylglycinate (19.6 mL, 105 mmol) was added. The mixture was stirred for 2 hours at 0° C. and at room temperature for 16 hours. The precipitate was removed by filtration, and anhydrous HCl was bubbled through the methylene chloride solution for 6 hours. The solvent was removed in vacuo, and the residue partitioned between ethyl acetate (3×300 mL) and 10% sodium bicarbonate (200 mL). The combined organic phases were washed with brine, dried over magnesium sulfate, filtered and evaporated to give Compound A as a white powder (36 g, 100%), mp: 140–143° C.

MS: $(M+H)^+345$.

B. 4-Phenylmethyl-1-[(1,1-dimethylethoxy)carbonyl]-2(S)-(2-hydroxyethyl)piperazine Lithium aluminum hydride (15.1 g, 377 mmol) was added portionwise to a mechanically stirred solution of Compound A (36.0 g, 105 mmol) in THF (780 mL). The reaction mixture was stirred at reflux for 18 hours, cooled to 0° C., and quenched by the sequential slow addition of water (20 mL), 10% NaOH (20 mL), water (20 mL), and diethylether (100 mL). The mixture was stirred at 0° C. for 30 minutes, at room temperature for 30 minutes and filtered. The solvent was removed in vacuo, the crude product taken up in methylene chloride (200 mL) and the solution dried over magnesium sulfate. The drying agent was removed by filtration, and the filtrate was treated with di-tert-butyl dicarbonate (25 g, 115 mmol). After 72 hours at room temperature, saturated sodium bicarbonate (300 mL) was added. The layers were separated, the aqueous phase reextracted with methylene chloride (300 mL), and the combined organic extracts dried over magnesium sulfate. Filtration and evaporation gave the crude product which was purified by flash chromatography on silica gel, eluting with 25% ethyl acetate in hexane. Compound B was obtained as a clear viscous oil (20 g, 60%).

MS: $(M+H)^+321$.

C. 4-Phenylmethyl-1-[(1,1-dimethylethoxy)carbonyl]-2(S)-(2-methoxyethyl)piperazine Compound B (6.18 g, 19.2 mmol) was dissolved in dry, degassed dimethylformamide and the solution was cooled to 0° C. under $N_2$. Sodium hydride (1.0 g, 24.9 mmol) was added followed by methyl iodide (3.8 g, 1.7 mL). After stirring for 3 hours at 0° C., saturated ammonium chloride was added. The mixture was concentrated under vacuum and the residue was partitioned between ethyl acetate and saturated sodium bicarbonate. The ethyl acetate layer was washed with water, brine and dried over $MgSO_4$. The crude product was chromatographed (silica gel, 40% ethyl acetate, 60% hexane) to yield Compound C as a clear oil (5.3 g, 82%).

MS: $(M+H)^+335$.

D. 1-[(1,1-Dimethylethoxy)carbonyl]-2(S)-(2-methoxyethyl)piperazine

Compound C (4.0 g, 12 mmol) was dissolved in methanol (49 mL) in a Parr bottle and the vessel was purged with Ar. To this was added 10% palladium on carbon and the reaction hydrogenated under 60 psi hydrogen for 16 hours. The catalyst was removed by filtration through Celite and the filtrate was concentrated under vacuum to yield Compound D as a clear oil (2.9 g, 99%).

MS: $(M+H)^+245$.

E. 1-[(1,1-Dimethylethoxy)carbonyl]-2(S)-(2-methoxyethyl)-4-(1-naphthalenylcarbonyl)piperazine A solution of 1-naphthoic acid (2.35 g, 13.1 mmol), 1-ethyl-3-(3-dimethylaminopropyl)carbodiimide.HCl (EDC, 2.74 g, 14.3 mmol), and 1-hydroxybenzotriazole (HOBT, 1.93 g, 14.3 mmol) were stirred in DMF (10 mL) at room temperature for 20 minutes. A solution of Compound D (3.0 g, 11.9 mmol) and N,N-diisopropylethylamine (DIEA, 3.5 g, 4.8 mL, 27.4 mmol) in DMF (10 mL) was added dropwise and the mixture was stirred for 16 hours. The mixture was poured into water (200 mL), and extracted with ethyl acetate (3×100 mL). The combined ethyl acetate layers were washed with water (2×100 mL), brine (100 mL), dried over $MgSO_4$ and concentrated. Chromatography on silica gel (40% ethyl acetate, 60% hexane) yielded Compound E as a slightly brown oil (4.8 g, 99%).

MS: $(M+H)^+399$.

F. 2(S)-(2-Methoxyethyl)-4-(1-naphthalenylcarbonyl)-piperazine, hydrochloride Compound E (240 mg, 0.60 mmol) was stirred in dimethyl sulfide (0.3 mL) and 4N HCl in dioxane (10 mL) for 30 minutes. The mixture was concentrated, redissolved in methylene chloride (50 mL) and concentrated. This procedure was repeated five times to yield Compound F as a clear glass.

G. (2S,4S)-[(1-[(1,1-dimethylethoxy)carbonyl]-4-[(triphenylmethyl)thio]-2-pyrrolidine carboxylic acid methyl ester To a solution of (2S,4R)-[(1-[(1,1-dimethylethoxy)carbonyl]-4-hydroxy-2-pyrrolidine carboxylic acid methyl ester (commercially available, 1.8 g, 7.3 mmol) and 2,6-di-t-butyl-4-methylpyridine (1.5 g, 7.3 mmol) in methylene chloride (27 mL) at 0° C. under nitrogen, was added triflic anhydride (1.4 mL, 8.1 mmol) in methylene chloride (7 mL) over 1 hour. The solution was stirred for an additional 15 minutes at 0° C. and added directly to a stirred solution of triphenylmethylmercaptan (4.9 g, 18 mmol) and 1M lithium hexamethyldisilazide in THF (18 mL, 18 mmol) in dry THF (30 mL) at 0° C. The mixture was warmed to room temperature and stirred for 16 hours, concentrated and the residue was chromatographed (260–400 mesh silica gel, 5.1×15 cm, 1:9–1:3/ethyl acetate:hexane). Fractions containing the desired product were concentrated to yield 1.5 g of Compound G as a glass. MS (M+H)⁺504.

H. (2S,4S)-[(1-[(1,1-dimethylethoxy)carbonyl]-4-[(triphenylmethyl)thio]-2-pyrrolidine carboxylic acid A solution of Compound G (0.50 g, 1.0 mmol) in THF (10 mL) and methanol (5 mL) was adjusted to pH 12 with 1N LiOH and stirred for 16 hours at room temperature. Ether (50 mL) was added along with water (30 mL) and the layers were separated. The aqueous layer was washed with ether (2×40 mL), acidified to pH 3–4 using 1N aqueous KHSO$_4$ and extracted again with ether (3×50 mL). The combined ether extracts from the acidic aqueous solution were dried (MgSO$_4$), pooled and concentrated to give 0.48 g of Compound H as a glass. MS (M+H)⁺489.

I. (2S,4S)-(N-methoxy-N-methylamino)-[(1-[(1,1-dimethylethoxy)carbonyl]-4-[(triphenylmethyl)thio]-2-pyrrolidine carboxlic acid amide Compound H (0.48 g, 1.0 mmol) was combined with N,O-dimethylhydroxylamine hydrochloride salt (100 mg, 1.1 mmol), PyBrop (510 mg, 1.1 mmol) and DIEA (540 μL, 3.1 mmol) in methylene chloride (30 mL) under argon at room temperature. The mixture was stirred for 2 hours and concentrated under vacuum. The residue was chromatographed (silica gel, 1:3–2:1/ethyl acetate:hexane) and fractions containing the desired compound were concentrated to yield 350 mg of Compound I as a glass. MS (M+H)⁺533.

J. (2S,4S)-[(1-[(1,1-dimethylethoxy)carbonyl]-4-[(triphenylmethyl)thio]-2-pyrrolidine carboxaldehyde Compound I (0.35 g, 0.65 mmol) was dissolved in dry THF (20 mL) and the solution was cooled to 0° C. 1M lithium aluminum hydride in THF (0.66 mL, 0.66 mmol) was added dropwise over 15 minutes. The mixture was stirred for 30 minutes at 0° C. under nitrogen. Ether (70 mL) was added, the mixture was quenched with dropwise addition of 1M KHSO$_4$ (10 mL) at 0° C. and stirred for 1 hour at 0° C. and the layers were separated. The organic layer was washed with 1M aqueous KHSO$_4$ (4×50 mL), aqueous saturated sodium bicarbonate (NaHCO$_3$) (50 mL) and brine (50 mL), dried (MgSO$_4$), and concentrated to yield Compound J as a white glass (270 mg) which was used immediately in the next step without further purification. R$_f$ 0.25 (ethyl acetate:hexane/1:1, UV, PMA).

K. [2S-[2a(R*),4a]]-1-[(1-[(1,1-Dimethylethoxy)carbonyl]-4-triphenylmethylmercapto-2-pyrrolidinyl)methyl]-2-(2-methoxyethyl)-4-(1-naphthalenylcarbonyl)piperazine Compound J (200 mg, 0.60 mmol) and compound F (240 mg, 0.520 mmol) were dissolved in dry methylene chloride (3 mL) and 1,2-dichloroethane (7 mL). Glacial acetic acid (0.5 mL) was added followed by sodium triacetoxyborohydride (160 mg, 0.78 mmol). The mixture was stirred for 16 hours, cooled to 0° C. and saturated sodium bicarbonate (2 mL) was added. The mixture was stirred for 20 minutes at 0° C., concentrated and partitioned between ethyl acetate (50 mL) and water (10 mL). The organic layer was separated and the aqueous layer was extracted with ethyl acetate (2×30 mL). The combined ethyl acetate phases were washed with water (60 mL), brine (50 mL), dried over MgSO$_4$ and concentrated. The crude product was chromatographed (silica gel, 40% ethyl acetate, 60% hexane) to yield Compound K as a clear oil (90 mg, 23%).

MS (M+H)⁺756.

L. [2S-[2a(R*),4a]]-1-[(4-Mercapto-2-pyrrolidinyl)methyl]-2-(2-methoxyethyl)-4-(1-naphthalenylcarbonyl)piperazine, trifluoroacetate A solution of Compound K (90 mg, 0.12 mmol) in methylene chloride (7 mL), triethylsilane (0.030 mL, 22 mg, 0.19 mmol), and trifluoroacetic acid (7 mL) was stirred for 1 hour at room temperature. The mixture was concentrated, triturated with hexanes and the remaining crude solid was purified by preparative HPLC (YMC S-10 ODS column, 30×500 mm; solvent A, 0.1% TFA in 90% water, 10% methanol; solvent B, 0.1% TFA in 10% water, 90% methanol; 20–50% B in 40 minutes, flow rate 20 mL/minute; UV monitored at 220 nm). Fractions containing the desired product were combined, concentrated and lyophilized to provide the compound of Example 1 as a white solid (25 mg, 33%), mp 85–86° C. [a]D$^{25}$=+22° (c=0.01, MeOH).

MS: (M+H)⁺414.

Analysis calculated for C$_{23}$H$_{31}$N$_3$O$_2$S.2.1 CF$_3$CO$_2$H. Calculated: C, 49.54; H, 5.04; N, 6.33. Found: C, 49.09; H, 5.17; N, 6.41.

EXAMPLE 2

[1a(S),3a]-1-[(3-Mercaptocyclopentyl)carbonyl]-2,2-methoxyethyl)-4-(1-naphthalenylcarbonyl)-piperazine

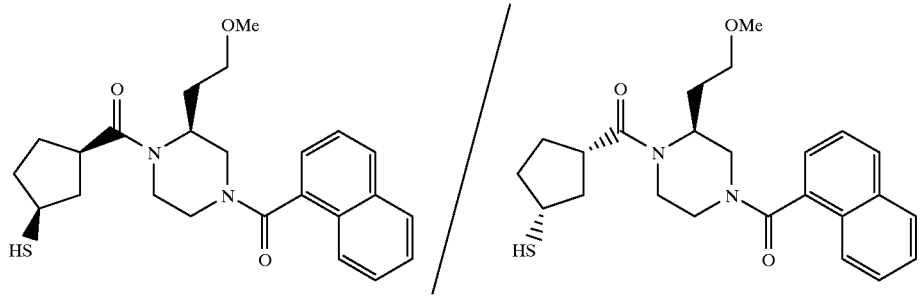

A. [1a(S),3a]-1-[(3-(Triphenylmethylthio) cyclopently)-carbonyl]-2-2-methoxyethyl)-4-(1-naphthalenylcarbonyl)-piperazine DIEA (0.23 mL, 1.3 mmol) was added to a solution of (±)-cis-3-[(triphenylmethyl)thio]cyclopentanecarboxylic acid [*Can. J. Chem.* 64, 2184, (1986)] (0.14 g, 0.36 mmol), Compound F of Example 1 (2(S)-(2-methoxyethyl)-4-(1-naphthalenylcarbonyl)-piperazine, hydrochloride; 0.13 g, 0.33 mmol), PyBrop (0.23 g, 0.33 mmol) and DMAP (0.61 g, 0.50 mmol) in $CH_2Cl_2$. The mixture was stirred 16 hours, quenched with 1N HCl (30 mL) and extracted with ethyl acetate (3×60 mL). The combined organic extracts were washed with 10% $NaHCO_3$ (1×50 mL) and the organnic layer was dried ($MgSO_4$), filtered and concentrated under vacuum. The residue was purified by flash chromatography (eluting with 2/1 hexane/acetone) to afford Compound A (0.19 g, 87%) as a glassy solid, mp: 86–91° C. MS: $(M+H)^+669$.

B. [1a(S),3a]-1-[(3-Mercaptocyclopentyl)carbonyl]-2,2-methoxyethyl)-4-(1-naphthalenylcarbonyl)piperazine All solvents used were degassed with argon. Triethylsilane (0.39 mL, 2.6 mmol) was added to a solution of Compound A (0.17 g, 0.26 mmol) in dicliloromethane (2 mL). TFA (2 mL was added and the mixture was stirred for 3 hours and concentrated under vacuum. The residue was triturated with hexane (3×10 mL) and the remaining residue was purified by preparative HPLC (YMC S10 ODS 30×500 mm, 30–90% aqeous methanol with 0.1% TFA, 60 minute gradient, 20 mL/minute) and the appropriate fractions were concentrated under vacuum. The residue was dissolved in water (5 mL), millipore filtered and lyophilized to afford the compound of Example 2 (0.04 g, 36%).

MS: $(M+H)^+427$.

IR (KBr) 2928, 2525, 1674, 1636, 1470, 1437, 1200, 1128 $cm^{-1}$. Analysis calculated for $C_{24}H_{30}N_2O_3S.0.2$ $CF_3CO_2H.0.69 H_2O$. Calculated: C, 63.45; H, 6.89; N, 6.06. Found: C, 63.45; H, 6.61; N, 6.01.

EXAMPLE 3

[1a(S),3a]-1-[(3-Mercaptocyclopentyl)methyl]-2-(2-methoxyethyl)-4-(1-naphthalenylcarbonyl)piperazine, monohydrochloride

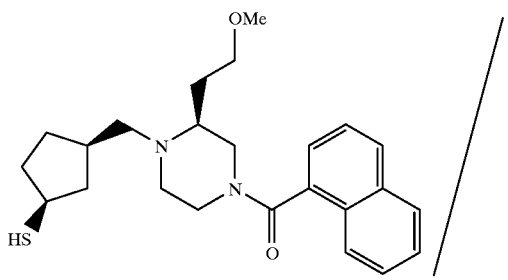

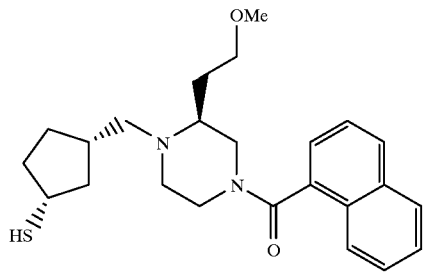

A. N,O-Dimethyl-cis-(3-(triphenylmethylthio) cyclopentyl)-hydroxamic acid

DIEA (1.2 mL, 7.1 mmol) was added to a solution of (±)-cis-3-[(triphenylmethyl)thio]cyclopentanecarboxylic acid (0.93 g, 2.4 mmol), BOP (1.0 g, 2.4 mmol) and N,O-dimethylhydroxylamine HCl (0.24 g, 2.4 mmol) in 3:1 $CH_3CN/DMF$. The mixture was stirred 16 hours, quenched with 1:1 10% LiCl/1N HCl (100 mL) and extracted with ethyl acetate (3×100 mL). The combined organic extracts were washed with 10% $NaHCO_3$ (1×50 mL), 10% LiCl (2×100 mL) and the organic layer was dried ($MgSO_4$), filtered and concentrated under vacuum. The residue was purified by flash chromatography (eluting with 2/1 hexane/acetone) to afford Compound A (0.9 g, 87%) as a glassy solid. MS: $(M+H)^+432$.

B. Cis-3-(triphenylmethylthio) cyclopentanecarboxaldehyde

Lithium aluminum hydride (1M, 2.4 mL, 2.4 mmol) was added to solution of Compound A (0.86 g, 2.0 mmol) in diethyl ether (30 mL) at −15° C. The mixture was stirred at −15° C. for 30 minutes and warmed to 0° C. and stirred for an additional 1 hour. The mixture was quenched with 10% $KHSO_4$ (10 mL) and the resulting mixture was stirred 1 hour at room temperature. The mixture was extracted with diethyl ether (3×50 mL). The combined organic extracts were washed with 10% $KHSO_4$ (1×100 mL), 10% $NaHCO_3$ (1×100 mL), dried ($MgSO_4$), filtered and concentrated under vacuum to afford Compound B (0.62 g, 84%) which was used without further purification. MS: $(M−H)^-$ 371.

C. [1a(S),3a]-1-[(3-(Triphenylmethylmercapto)-cyclopentyl)methyl]-2-(2-methoxyethyl)-4-(1-naphthalenylcarbonyl)piperazine Sodium triacetoxyborohydride (0.35 g, 1.7 mmol) was added to a mixture of Compound B (0.40 g, 1.1 mmol) and Compound F of Example 1 (2(S)-(2-methoxyethyl)-4-(1-naphthalenylcarbonyl)piperazine, hydrochloride) in $CH_2Cl_2$ (10 mL). The mixture was stirred for 2 hours and quenched with 10% $NaHCO_3$ (50 mL). The biphasic solution was extracted with $CH_2Cl_2$ (3×50 mL) and the combined organic extracts were dried ($MgSO_4$), filtered and concentrated under vacuum. The residue was purified by flash chromatography (eluting with 1/1 hexane/ethyl acetate) to afford Compound C (0.5 g, 80%) as a glassy solid. MS: $(M+H)^+$ 655.

D. [1a(S),3a]-1-[(3-Mercaptocyclopentyl)methyl]-2-(2-methoxyethyl)-4-(1-naphthalenylcarbonyl)piperazine, monohydrochloride The title compound was prepared from Compound C as described for Compound B of Example 2. Following prep HPLC, the residue was dissolved in methanol (5 mL) and 1N HCl (1 mL) was added. The mixture was stirred 5 minutes and concentrated under vacuum. This latter procedure was repeated two times and the residue was dissolved in water (5 mL), millipore filtered and lyophilized to afford Example 3 as a white solid, mp: 88–98° C.

MS: $(M+H)^+413$.

Analysis calculated for $C_{24}H_{32}N_2O_2S \cdot 1.0 HCl \cdot 0.88 H_2O$. Calculated: C, 62.00; H, 7.54; N, 6.03. Found: C, 62.00; H, 7.62; N, 5.96.

EXAMPLE 4

[2S-[2a(R*),4a]]-1-[(4-Mercapto-2-pyrrolidinyl) methyl]-4-(1-naphthalenylcarbonyl)-2-[2-(3-pyridinylmethoxy)ethyl]piperazine, trifluoroacetate

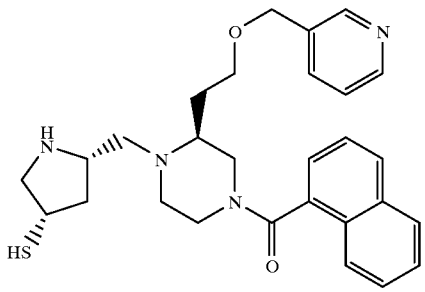

A. 1-[(1,1-dimethylethoxy)carbonyl]-2(S)-(2-hydroxyethyl)-piperazine

10% Pd/C (0.38 g) was added to a solution of Compound B of Example 1 (4-phenylmethyl-1-[(1,1-dimethylethoxy) carbonyl]-2(S)-(2-hydroxyethyl)piperazine; 2.1 g, 6.56 mmol) in MeOH (30 mL) at room temperature. The mixture was agitated under hydrogen atmosphere at 53 psi for 20 hours and filtered through a celite pad. The pad was washed 3 times with methanol. The filtrate was concentrated to afford Compound A as a viscous oil (1.58 g, 100%). MS: $(M+H)^+231$.

B. 1-[(1,1-Dimethylethoxy)carbonyl]-2(S)-(2-hydroxyethyl)-4-(1-naphthalenylcarbonyl)piperazine Compound B was prepared from Compound A as described for Compound E of Example 1. MS: $(M+H)^+385$.

C. 1-[1,1-Dimethylethoxy)carbonyl]-2(S)-[2-((3-pyridinylmethoxy)ethyl)]-4-(1-naphthalenylcarbonyl)-piperazine NaH (0.79 g, 20.8 mmol) was added to a solution of Compound B (0.8 g, 2.0 mmol) in DMF (16 mL) at room temperature under argon. After stirring for 0.5 hour, picolyl chloride (1.64 g, 10 mmol) was added. The mixture was heated at 93° C. for 5 hours and the DMF was evaporated. The residue was diluted with saturated $NH_4Cl$ solution (30 mL) and EtOAc (50 mL). The aqueous layer was reextrated with EtOAc (2×50 mL). The combined organic layers were washed with $NH_4Cl$, $NaHCO_3$, $H_2O$, NaCl (3×30 mL), dried over $MgSO_4$, fitered and concentrated. Flash chromatography (silica, EtOAc) afforded Compound C. (0.70 g, 74%). MS: $(M+H)^+476$.

D. [2S-[2a(R*),4a]]-1-[(1-[(1,1-Dimethylethoxy) carbonyl]-4-triphenylmethylmercapto-2-pyrrolidinyl)methyl]-2-((3-pyridinylmethoxy) ethyl)]-4-(1-naphthalenylcarbonyl)-piperazine TFA (5 mL) was added to a solution of Compound C (0.35 g, 0.74 mmol) in $CH_2Cl_2$ (5 mL). The mixture was stirred 30 minutes and concentrated. The residue was extracted with $CHCl_3$ (2×15) and the combined extractes were concentrated to afford Compound D.

E. [2S-[2a(R*),4a]]-1-[(1-[(1,1-Dimethylethoxy) carbonyl]-4-triphenylmethylmercapto-2-pyrrolidinyl)methyl]-2-((3-pyridinylmethoxy) ethyl)]-4-(1-naphthalenylcarbonyl)-piperazine Thiethylamine was added to a solution of Compound D in $CH_2Cl_2$ (2 mL) and the pH was adjusted to 7. A solution of the title J compound of Example 1 ((2S,4S)-[(1-[(1,1-dimethylethoxy)carbonyl]-4-triphenylmethylthio-2-pyrrolidine carboxaldehyde; 0.34 g, 0.72 mmol) in $CH_2Cl_2$ (2 mL) was added to the above solution, followed by 3A sieves (5 g). The mixture was stirred for 15 minutes under argon. Sodium triacetoxyborohydride (0.63 g, 2.97 mmol) was added. The mixture was stirred for 16 hours and diluted with EtOAc (30 mL) and $NaHCO_3$ (10 mL). The layers were separated and the aqueous layer was reextracted with EtOAc (2×20 mL). The combined organic layers were combined and washed with $NaHCO_3$ (20 mL), NaCl (2×20 mL), dried over $MgSO_4$, filtered and concentrated. Flash chromatography (silica, step gradient of hexane and EtOAc followed by 9/1 $CHCl_3$/MeOH) afforded Compound E (0.15 g, 26%) as a foamy solid. MS: $(M+H)^+833.5$.

F. [2S-[2a(R*),4a]]-1-[(4mercapto-2-pyrrolidinyl) methyl]-2-((3-pyridinylmethoxy)ethyl)]-4-(1-naphthalenylcarbonyl)-piperazine Compound F was prepared from Compound E as described for Compound L of Example 1.

MS: $(M+H)^+491$.

EXAMPLE 5

[2S-[2a(R*),4β]]-1-[(4-Mercapto-2-pyrrolidinyl) methyl]-2-(2-methoxyethyl)-4(1-naphthalenylcarbonyl)piperazine, dihydrochloride

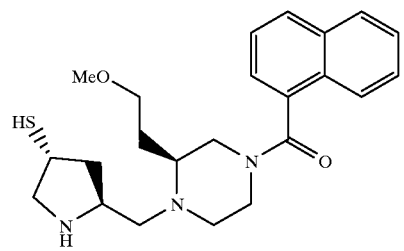

A. (2S,4R)-[(1-[(1,1-dimethylethoxy)carbonyl]-4-[(triphenylmethyl)thio]-2-pyrrolidine carboxylic acid methyl ester Compound A was prepared in a similar manner to Compound G in Example 1 starting with (2S,4R)-[(1-[(1,1-dimethylethoxy)carbonyl]-4-hydroxy-2-pyrrolidine carboxylic acid methyl ester (commercially available). Yield 1.5 g of Compound A as a glass. MS $(M+H)^+504$.

B. (2S,4R)-[(1-[(1,1-dimethylethoxy)carbonyl]-4-((triphenylmethyl)thio]-2-pyrrolidine carboxylic acid Compound B was prepared in a similar manner to Compound H in Example 1 starting with Compound A. Yield 0.48 g of Compound B as a glass. MS $(M+H)^+489$.

C. (2S,4R)-(N-methoxy-N-methylamino)-[(1-[(1,1-dimethylethoxy)carbonyl]-4-[(triphenylmethyl)thio]-2-pyrrolidine carboxylic acid amide Compound C. was prepared in a similar manner to Compound I in Example 1 starting with Compound B. Yield: 350 mg of Compound C as a glass. MS (M+H)⁺533.

D. (2S,4R)-[(1-[(1,1-dimethylethoxy)carbonyl]-4-[(triphenylmethyl)thio]-2-pyrrolidine carboxaldehyde Compound D was prepared in a similar manner to Compound J in Example 1 starting with Compound C Yield: 270 mg of Compound D as a glassy solid which was used immediately in the next step without further purification. $R_f$ 0.25 (ethyl acetate:hexane/1:1, UV, PMA).

E. [2S-[2a(R*),4b]]-1-[(4-Mercapto-2-pyrrolidinyl)methyl]-2-(2-methoxyethyl)-4-(1-naphthalenylcarbonyl-piperazine, dihydrochloride The title compound was prepared from Compound D by the procedure of Compound K of Example 1 followed by the procedure of Compound L of Example 1 except that the HPLC purified compound was dissolved in 1N HCl followed by removal of solvent using lyophilization and this procedure repeated to provide 40 mg (38%) of the compound of Example 5 as a white powder. mp 152–153° C.

MS (M+H)⁺414. Analysis calculated for $C_{23}H_{31}N_3O_2S.2.4HCl$, $1.1H_2O$. Calculated: C 53.03, H 6.89, N 8.07, Found: C 53.09, H 6.86, N 7.73.

EXAMPLE 6

[2R-[2a(S*),4β]]-1-[(4Mercapto-2-pyrrolidinyl)methyl]-2-(2methoxyethyl)-4-(1-naphthalenylcarbonyl)piperazine, dihydrochloride

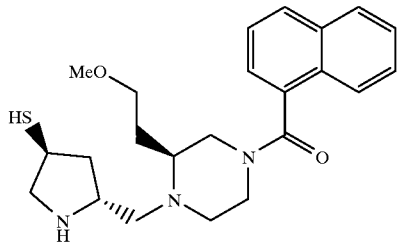

A. (2R,4R)-[(1-[(1,1dimethylethoxy)carbonyl]-4-hydroxy-2-pyrrolidine carboxylic acid A solution of di-t-butyl-di-carbonate (40 g, 0.18 mol) in p-dioxane (200 mL) was added dropwise to a solution of (2R,4R)-4-hydroxy-2-pyrrolidine carboxylic acid (20 g, 0.15 mol) in 10% NaHCO₃ (200 mL) in water over 1 hour and the solution was stirred at 0° C. for 20 minute. The solution was allowed to warm to room temperature and stirred for additional 40 hours, concentrated and the resulting aqueous layer was extracted with ethyl acetate (3×300 mL). The organic layers were combined, washed with brine; dried (MgSO₄) and concentrated to yield Compound A as a white solid (20 g, 57%). MS (M+H)⁺232.

B. (2R,4R)-[(1-[1,1-dimethylethoxy)carbonyl]-4-hydroxy-2-pyrrolidine carboxylic acid, methyl ester To a solution of Compound A (13 g, 56.22 mmol) in methanol (130 mL) was slowly added 2M trimethylsilyl-diazomethane in hexane (37 mL, 73 mmol). The mixture was stirred for 1 hour and concentrated under vacuum to afford 14 g of Compound B. MS (M+H)⁺246.

C. [2R-[2a(S*),4b]]-1-[(4-Mecapto-2-pyrrolidinyl)methyl]-2-(2-methoxyethyl)-4-(1-naphthalenylcarbonyl)piperazine, dihydrochloride The title compound was prepared from Compound B by following the procedures outlined for Compounds G through L of Example 1. The HPLC purified compound was dissolved in 1N HCl followed by removal of solvent using lyophilization. This procedure was repeated to provide the compound of Example 6 as a white powder. mp 144–145° C., MS (M+H)⁺414. Analysis calculated for $C_{23}H_{31}N_3O_2S.2.0HCl$, $1.4H_2O$. Calculated: C 53.99, H 7.05, N 8.21, Cl 13.86, Found: C 54.14, H 7.00, N 8.09, 14.14.

EXAMPLE 7

[2S-[2a(R*),4a]]-1-[(4-Mercapto-2-pyrrolidinyl)methyl]-4(1-naphthalenylcarbonyl)piperazine, dihydrochloride

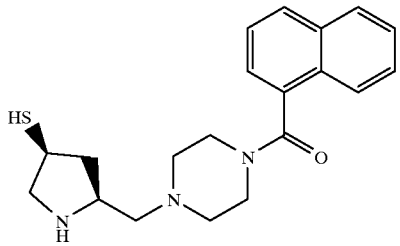

The title compound was prepared from piperazine using the following procedure: Compound A of Example 6, with chromatography on silica using 1:9–1:3/ethyl acetate:hexane; coupling with 1-naphthoic acid as described for Compound E of Example 1 and Compound F of Example 1; with (2S,4S)-[(1-[(1,1-dimethylethoxy)carbonyl]-4-triphenylmethylmercapto-2-pyrrolidine carboxaldehyde as described in Compound K of Example 1; Compound L of Example 1, except the HPLC purified compound was dissolved in 1N HCl followed by removal of solvent using lyophilization and this procedure was repeated to provide 180 mg (70 %) of the compound of Example 7 as a white powder, mp 189–190° C.

MS (M+H)⁺356. Analysis calculated for $C_{20}H_{25}N_3OS.2.0HCl$, $1.1H_2O$: Calculated: C 53.59, H 6.56, N 9.37, Found: C 53.67, H 6.26, N 9.27, [a]D+20.7 (c=0.6, methanol).

23

EXAMPLE 8

[2S-[2a(R*),4a]]-1-[(4-Mercapto-2-pyrrolidinyl)methyl]-4-(1-naphthalenylcarbonyl)-2-[2-(phenylsulfony)ethyl]piperazine, trifluroacetate

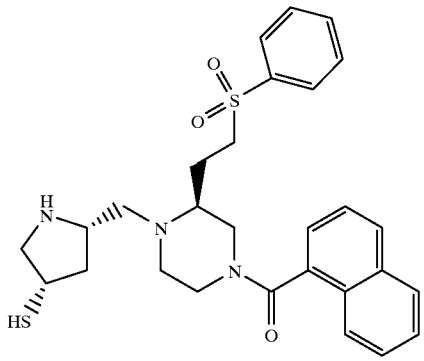

A. 1-[(1,1-Dimethylethoxy)carbonyl]-4-(1-napthalenylcarbonyl-2(S)-(2-hydroxyethyl)piperazine A mixture of Compound B of Example 1 (4-phenylmethyl-1[(1,1-dimethylethoxy)carbonyl]-2(S)-(2-hydroxyethyl)piperazine; 1.05 g, 3.28 mmol), Palladium hydroxide (500 mg, 20% on carbon), and methanol (80 mL) was hydrogenated at 60 psi for 18 hours, filtered and concentrated in vacuo. The residue was dissolved in DMF. Naphthoic acid (775 mg, 4.5 mmol), EDC (865 mg, 4.5 mmol), 1-hydroxybenzotriazole (607 mg, 4.5 mmol), and triethylamine (1.4 mL, 4.5 mmol) were added, and the mixture was stirred for 18 hours. The mixture was poured into saturated aqueous sodium bicarbonate solution, extracted with ethyl acetate (2x), washed with water and brine, dried, and concentrated. The residue was purified by flash chromatography on silica gel (300 g), eluting with 1:1 hexane: ethyl acetate, to give Compound A as an oil (700 mg, 58%).

B. 1-[(1,1-Dimethylethoxy)carbonyl]-4-(1-napthalenylcarbonyl)-2(S)-(2-phenylthioethyl)piperazine To a mixture of Compound A (600 mg, 1.63 mmol) and tetrahydrofliran (5 mL) were added diphenyldisulfide (720 mg, 3.3 mmol) and tri-n-butyl phosphine (870 μl, 3.3 mmol). The resulting mixture was stirred for 18 hours and poured into saturated aqueous sodium bicarbonate solution. The solution was extracted with ethyl acetate (2x), washed with 1N sodium hydroxide solution (2x), dried, and concentrated. The residue was combined with similar material from a 0.16 mmol scale reaction and purified by flash chromatography on silica gel (200 g), eluting with 2:1 hexane:ethyl acetate, to Compound B as a clear oil (800 mg, 94%).

C. 1-[(1,1-Dimethylethoxy)carbonyl]-4-(1-napthalenylcarbonyl)-2(S)-(2-phenylsulfonylethyl)piperzine Monoperoxyphthalic acid magnesium salt (2.5 g, 4 mmol) was added to a mixture of Compound B (600 mg, 1.26 mmol) and methanol (5 mL) at 0° C. The mixture was stirred for 2 hours as it slowly warmed to room temperature. Excess sodium thiosulfate solution was added and the mixture was stirred for 10 minutes and poured into saturated aqueous sodium bicarbonate solution, extracted with ethyl acetate (2x), washed with water and brine, dried, and concentrated to give Compound C (510 mg, 80%).

D. 4-(1-Napthalenylcarbonyl)-2(S)-(2-phenylsulfonylethyl)-piperazine

A mixture of Compound C (560 mg, 1.1 mmol), TFA (5 mL), and methylene chloride (5 mL) was stirred at room temperature for 2 hours and concentrated in vacuo to give Compound D (210 mg, 37%).

E. 1-[(1,1-Dimethylethoxy)carbonyl]-4-(1-naphthalenylcarbonyl)-2(S)-(2-phenylsulfonylethyl)-piperazine Compound E was prepared from Compound D as outlined for Compound K in Example 1. Yield:190 mg (52%).

F. [2S-[2a(R*),4a]]-1-[(4-Mercapto-2-pyrrolidinyl)methyl]-4-(1-naphthalenylcarbonyl)-2-[2-(phenylsulfonyl)ethyl]-piperazine, trifluoroacetate The title compound was prepared from Compound E as outlined for Compound L in Example 1. Yield: 56 mg of white powder (36%).

MS (M+H)$^+$524. Analysis calculated for $C_{28}H_{33}N_3O_3S_2$1.2 TFA, 0.6 H$_2$O: Calculated: C 54.00; H 5.26; N, 6.16; F, 10.66; S, 9.44, Found: C 54.00; H 5.22, N, 6.05; F, 10.69; S, 9.41.

What is claimed is:

1. A compound of the formula

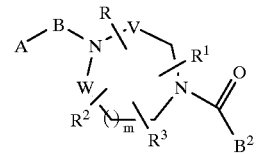

its enantiomers, diastereomers, or pharmaceutically acceptable salts, or solvates thereof where A is

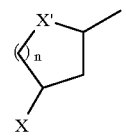

optionally substituted, at any available position or positions on the ring, with one or more of the following substituents, halo, alkyl, alkoxy, aryl, hydroxy, alkanoyl, alkanoyloxy, amino, alkylamino, dialkylamino, alkanoylamino, thio], alkylthio, alkylthiono, alkylsulfonyl, sulfonamido, nitro, cyano, carboxy, carbamyl or alkoxycarbonyl;

B is —CH$_2$— or —C(O)—;

B$^2$ is alkyl, aryl or heterocycle;

V and W are each, independently, —CH$_2$— or —C(O)—;

X is —SH, —OH or —NHR$^6$;

X' is —NR$^7$—, —CH$_2$— or —CH(NHR$^8$)—;

R, R$^1$, R$^2$ and R$^3$ are each independently, hydrogen, alkyl, alkenyl, alkynyl, aryl, heterocycle, —C(O)NR$^4$R$^5$, or —C(O)OR$^4$; or any two of R, R$^1$, R$^2$ and R$^3$, if present, may also be alkylene attached to the same carbon atom forming a spiro ring;

R$^4$ and R$^5$ are each independently selected from hydrogen, hydroxyl, alkyl, cycloalkyl, heterocycle, aryl, aroyl, heteroaroyl, arylsulfonyl or heteroarylsulfonyl; or $R^4$ and $R^5$ may together form a 5- to 7-membered saturated ring with the atom to which they are attached; said ring being optionally substituted with halogen, hydroxy, alkoxy, oxo, nitro, cyano, —C(O)H, —C(O)OH and the like;

$R^6$, $R^7$ and $R^8$ are each independently, hydrogen or alkyl;

m is 0; and n is an integer from 1 to 2.

2. A compound of claim 1 wherein A is

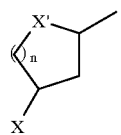

B is —CH$_2$— or —C(O)—;

$B^2$ is aryl;

V and W are each, independently, —CH$_2$—;

X is —SH;

X' is —NR$^7$— or —CH$_2$—; and $R^7$ is hydrogen or alkyl.

3. A compound of claim 1, wherein A is

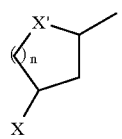

B is —CH$_2$—;

$B^2$ is aryl;

V and W are each, independently, —CH$_2$—;

X is —SH;

X' is —NR$^7$— or —CH$_2$—; and $R^7$ is hydrogen or alkyl.

4. A compound of claim 1 wherein A is

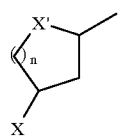

B is —C(O)—;

$B^2$ is aryl;

V and W are each, independently, —CH$_2$—;

X is —SH;

X' is —NR$^7$— or —CH$_2$—; and $R^7$ is hydrogen or alkyl.

5. A compound of claim 1 wherein A is

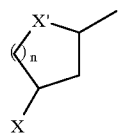

B is —CH$_2$— or —C(O)—;

$B^2$ is aryl;

V and W are each, independently, —CH$_2$—;

X is —SH;

X' is —NR7— or —CH$_2$—;

R is alkyl;

$R^1$, $R^2$ and $R^3$ are each hydrogen;

$R^7$ is hydrogen or alkyl;

m is 0; and n is 1.

6. A compound of claim 1 wherein A is

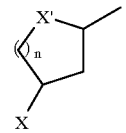

B is —CH$_2$—;

$B^2$ is aryl;

V and W are each, independently, —CH$_2$—;

X is —SH;

X' is —NR'— or —CH$_2$—;

R is alkyl;

$R^1$ $R^2$ and $R^3$ are each hydrogen;

$R^7$ is hydrogen or alkyl;

m is 0; and n is 1.

7. A compound of claim 1 wherein A is

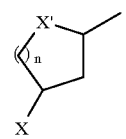

B is —C(O)—;

$B^2$ is aryl;

V and W are each, independently, —CH$_2$—;

X is —SH;

X' is —NR$^7$— or —CH$_2$—;

R is alkyl;

$R^1$, $R^2$ and $R^3$ are each hydrogen;

$R^7$ is hydrogen or alkyl;

m is 0; and n is 1.

8. A compound of claim 1 wherein A is

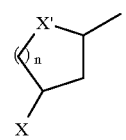

B is —CH$_2$— or —C(O)—;

$B^2$ is aryl;

V and W are each, independently, —CH$_2$—;

X is —SH;

X' is —NR$^7$— or —CH$_2$—;

$R^1$, $R^2$ and $R^3$ are each hydrogen;

$R^7$ is hydrogen or alkyl;
m is 0; and
n is 1.

9. A compound of claim 1 wherein A is

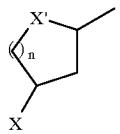

B is —$CH_2$— or —C(O)—;
$B^2$ is aryl;
V and W are each, independently, —$CH_2$—;
X is —SH;
X' is —$NR^7$— or —$CH_2$—;
$R^1$, $R^2$ and $R^3$ are each hydrogen;
$R^7$ is hydrogen or alkyl;
m is 0; and
n is 1.

10. A compound of claim 1 which is
[2S-[2a(R*),4a]]-1-[(4-mercapto-2-pyrrolidinyl)methyl]-2-(2-methoxyethyl)-4-(1-naphthalenylcarbonyl) piperazine, trifluoroacetate;
[1a(S),3a]-1-[(3-mercaptocyclopentyl)carbonyl]-2-2-methoxyethyl)-4-(1-naphthalenylcarbonyl)piperazine;
[1a(S),3a]-1-[(3-mercaptocyclopentyl)methyl]-2-(2-methoxyethyl)-4-(1-naphthalenylcarbonyl)piperazine, monohydrochloride;
[2S-[2a(R*),4a]]-1-[(4-mercapto-2-pyrrolidinyl)methyl]-4-(1-naphthalenylcarbonyl)-2-[2-(3-pyridinylmethoxy) ethyl]-piperazine, trifluoroacetate;
[2S-[2a(R*),4β]]-1-[(4-mercapto-2-pyrrolidinyl)methyl]-2-(2-methoxyethyl)-4-(1-naphthalenylcarbonyl) piperazine, dihydrochloride;
[2R-[2a(S*),4β]]-1-[(4-mercapto-2-pyrrolidinyl)methyl]-2-(2-methoxyethyl)-4-(1-naphthalenylcarbonyl) piperazine, dihydrochloride;
[2S-[2a(R*),4a]]-1-[(4-mercapto-2-pyrrolidinyl)methyl]-4-(1-naphthalenylcarbonyl)piperazine, dihydrochloride;
[2S-[2a(R*),4a]]-1-[(4-mercapto-2-pyrrolidinyl)methyl]-4-(1-naphthalenylcarbonyl)-2-[2-(phenylsulfonyl) ethyl]-piperazine, trifluoroacetate; or
a pharmaceutically acceptable salt thereof.

11. A method of inhibiting farnesyl protein transferase which comprises administering to a mammalian subject an effective farnesyl protein transferase inhibiting amount of a compound of claim 1.

12. A method of inhibiting prenyl transferases which comprises administering to a mammalian subject an effective prenyl transferase inhibiting amount of a compound of claim 1.

13. A method of inhibiting tumors which comprises administering to a mammalian subject an effective tumor inhibiting amount of a compound of claim 1.

14. A method of treating diseases associated with signal transduction pathways operating through Ras which comprises administering to a mammalian subject an amount of a compound of claim 1 effective for treating said diseases.

15. A method of treating diseases associated with proteins that are post-translationally modified by the enzyme farnesyl protein transferase which comprises administering to a mammalian subject an amount of a compound of claim 1 effective for treating said diseases.

16. A method of treating diseases associated with proteins that are post-translationally modified by the enzymes geranylgeranyl protein transferase which comprises administering to a mammalian subject an mount of a compound of claim 1 effective for treating said diseases.

17. A method of treating autoimmune diseases which comprises administering to a mammalian subject an amount of a compound of claim 1 effective for treating said diseases.

18. A pharmaceutical composition comprising a pharmaceutical carrier and a therapeutically effective amount of a compound of claim 1.

* * * * *